United States Patent
Perche et al.

(10) Patent No.: US 10,207,059 B2
(45) Date of Patent: Feb. 19, 2019

(54) DEVICE FOR RECEIVING AN INJECTION SYRINGE COMPRISING A PROTECTIVE CAP FOR THE NEEDLE

(71) Applicants: Patrick Perche, Mions (FR); Philippe Sahm, Aix les Bains (FR); Clement Dumet, Vaulx en Velin (FR); Jose Camba, Amberieu en Bugey (FR); Pascal Dugand, Estrablin (FR); Nemera La Verpilliére S.A.S, La Verpilliere (FR)

(72) Inventors: Patrick Perche, Mions (FR); Philippe Sahm, Aix les Bains (FR); Clement Dumet, Vaulx en Velin (FR); Jose Camba, Amberieu en Bugey (FR); Pascal Dugand, Estrablin (FR)

(73) Assignee: Nemera la Verpilliere (FR)

( * ) Notice: Subject to any disclaimer, the term of this patent is extended or adjusted under 35 U.S.C. 154(b) by 0 days.

(21) Appl. No.: 15/026,179

(22) PCT Filed: Sep. 17, 2014

(86) PCT No.: PCT/FR2014/052315
§ 371 (c)(1),
(2) Date: Mar. 30, 2016

(87) PCT Pub. No.: WO2015/044561
PCT Pub. Date: Apr. 2, 2015

(65) Prior Publication Data
US 2016/0243315 A1 Aug. 25, 2016

(30) Foreign Application Priority Data

Sep. 30, 2013 (FR) ...................................... 13 59458

(51) Int. Cl.
*A61M 5/32* (2006.01)
*A61M 5/46* (2006.01)

(52) U.S. Cl.
CPC .......... *A61M 5/3204* (2013.01); *A61M 5/326* (2013.01); *A61M 5/46* (2013.01); *A61M 2205/586* (2013.01); *A61M 2207/00* (2013.01)

(58) Field of Classification Search
CPC ........ A61M 2205/586; A61M 2207/00; A61M 5/3204; A61M 5/326; A61M 5/46
See application file for complete search history.

(56) References Cited

U.S. PATENT DOCUMENTS 5,137,516 A * 8/1992 Rand .......................... A61J 1/00
604/136
6,585,702 B1 * 7/2003 Brunel ................ A61M 5/3202
604/198

(Continued)

FOREIGN PATENT DOCUMENTS

EP 2468340 A1 6/2012
FR 2654938 A1 5/1991

(Continued)

*Primary Examiner* — Quynh-Nhu H. Vu
(74) *Attorney, Agent, or Firm* — St. Onge Steward Johnston & Reens, LLC

(57) ABSTRACT

A device for receiving an injection syringe, configured to receive an injection syringe including a needle and a protective cap for the needle. The receiving device has a distal end and includes a member for removing the protective cap, removably fastened onto the distal end of the receiving device, the removal member including a gripping section for gripping by a user and a catch on the cap, able to drive the cap when the removal member is removed from the receiving device, so as to strip the needle. An assembly including a receiving device and an injection syringe as well as a method for assembling a receiving device and an injection syringe.

15 Claims, 5 Drawing Sheets

(56) References Cited

U.S. PATENT DOCUMENTS

| | | | |
|---|---|---|---|
| 7,635,356 B2 * | 12/2009 | Stamp | A61M 5/2033 604/117 |
| 2002/0095120 A1 * | 7/2002 | Larsen | A61M 5/2033 604/187 |
| 2010/0016793 A1 * | 1/2010 | Jennings | A61M 5/2033 604/134 |
| 2010/0185178 A1 * | 7/2010 | Sharp | A61M 5/002 604/506 |
| 2012/0191047 A1 * | 7/2012 | Raday | A61M 5/2033 604/198 |
| 2013/0281938 A1 * | 10/2013 | Ekman | A61M 5/20 604/198 |

FOREIGN PATENT DOCUMENTS

| | | |
|---|---|---|
| FR | 2830765 A1 | 4/2003 |
| GB | 2410188 A | 7/2005 |
| WO | 2009040607 A1 | 4/2009 |
| WO | 2013006119 A1 | 1/2013 |

* cited by examiner

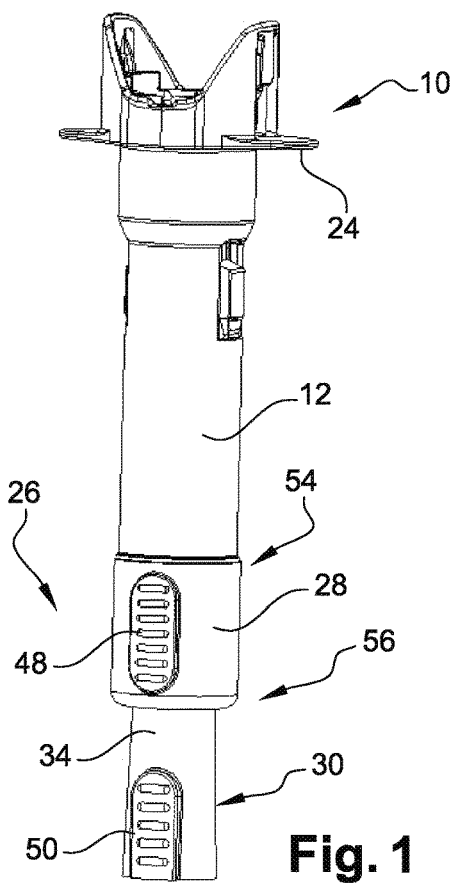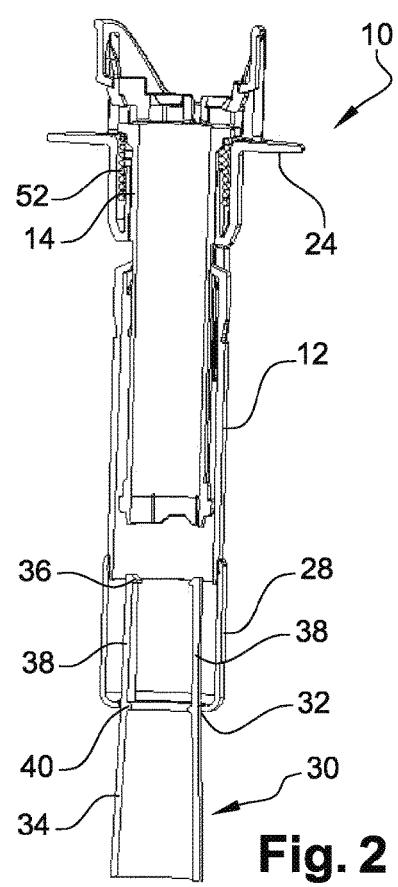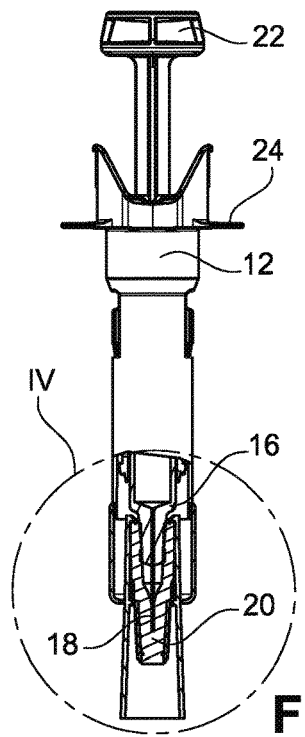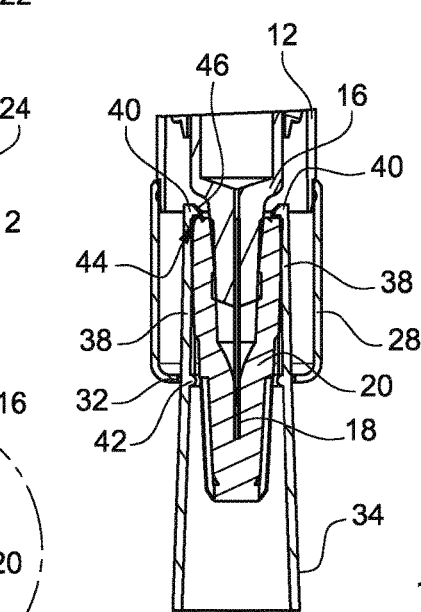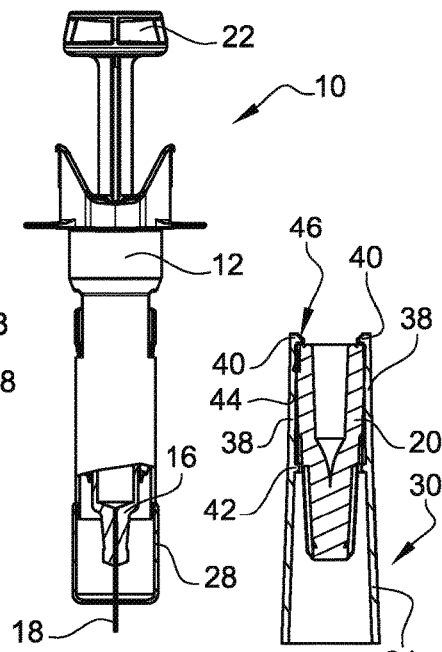
Fig. 1  Fig. 2  Fig. 3  Fig. 4  Fig. 5  Fig. 6

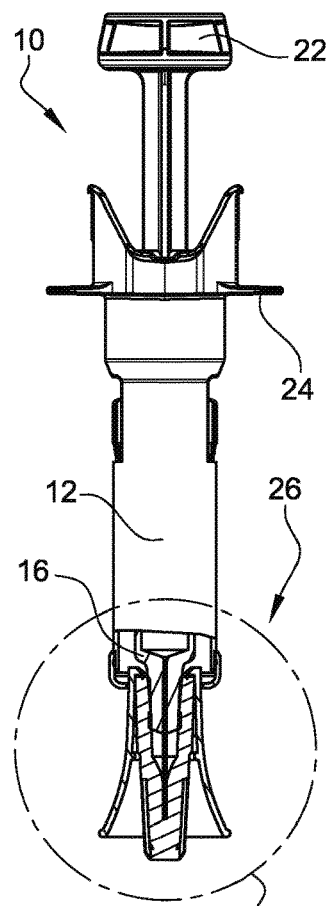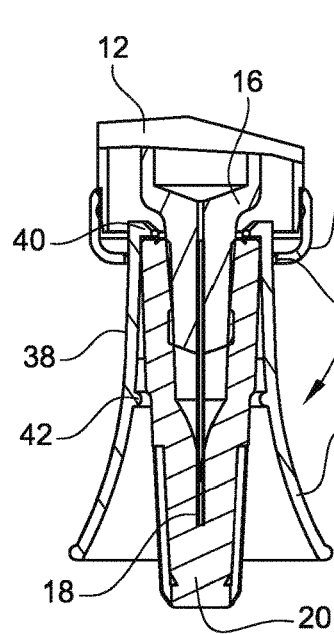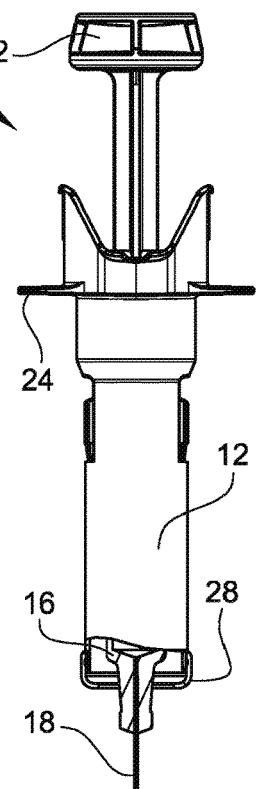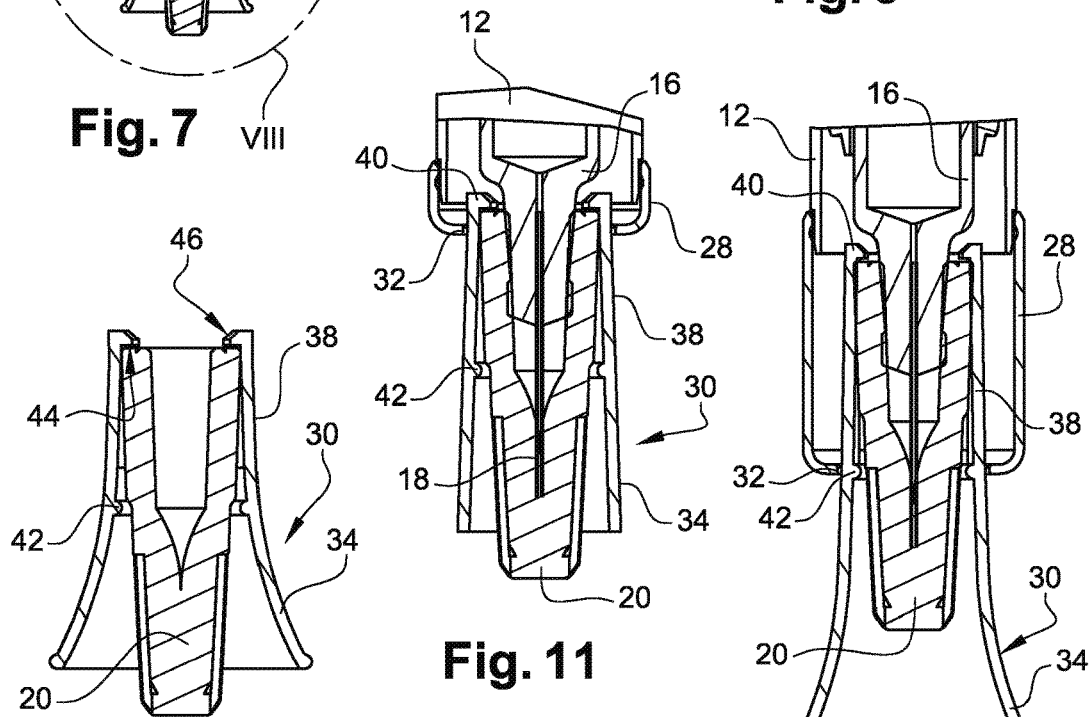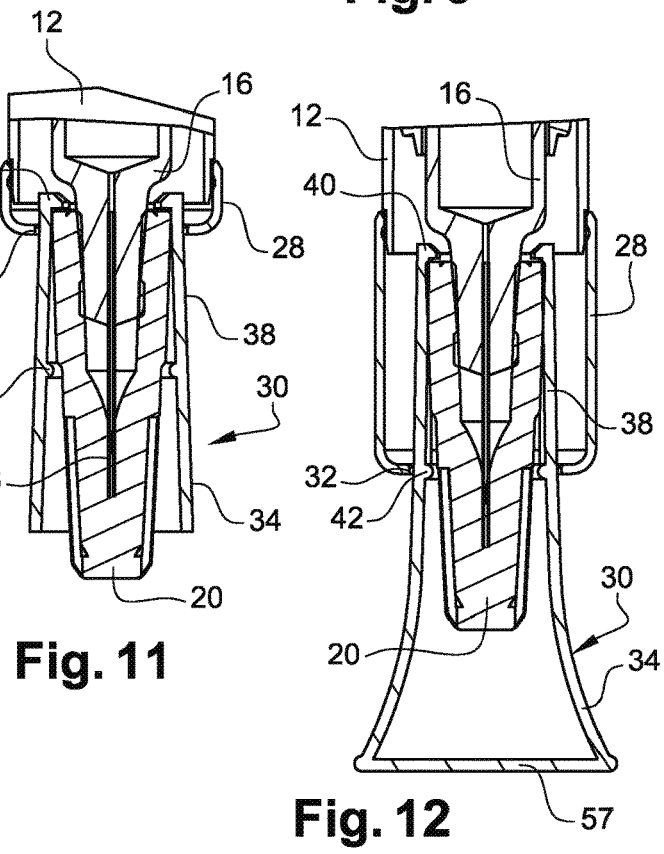
Fig. 7
Fig. 8
Fig. 9
Fig. 10
Fig. 11
Fig. 12

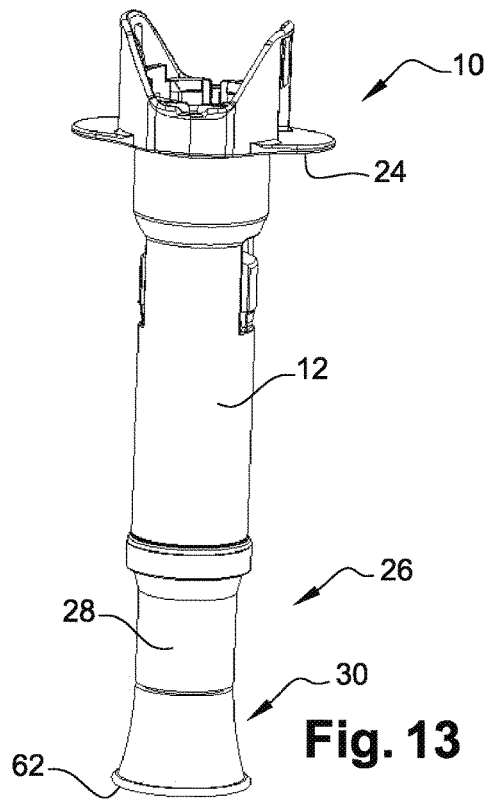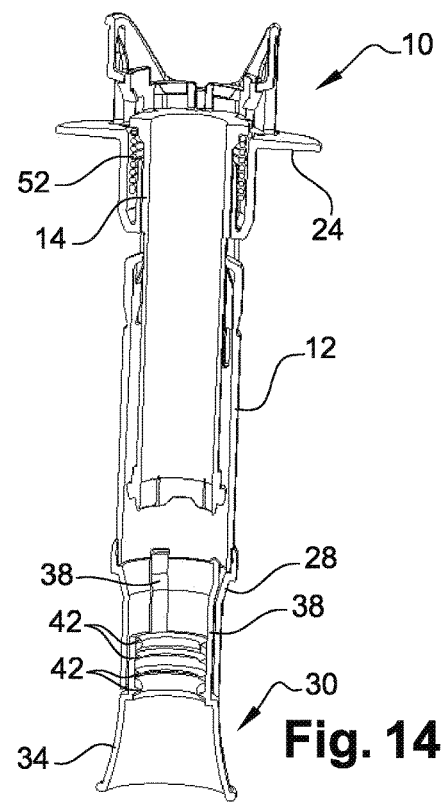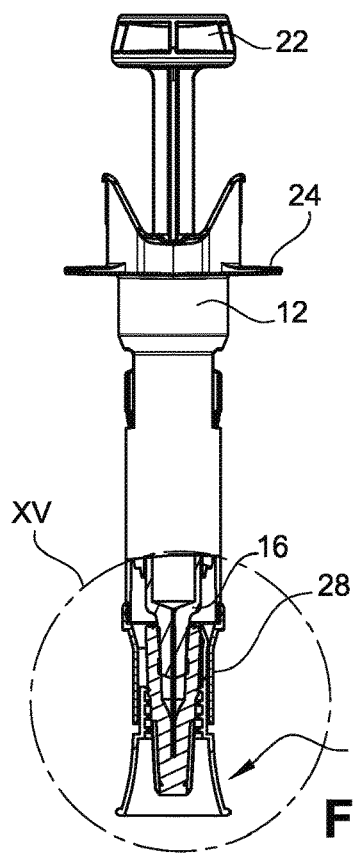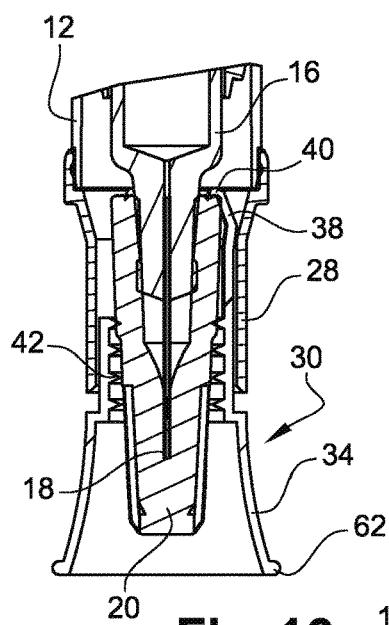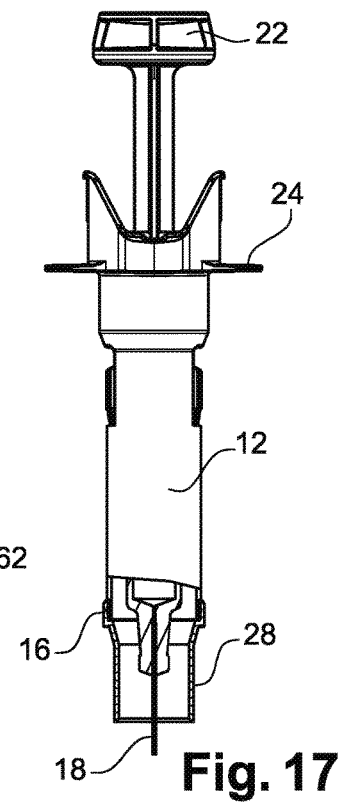

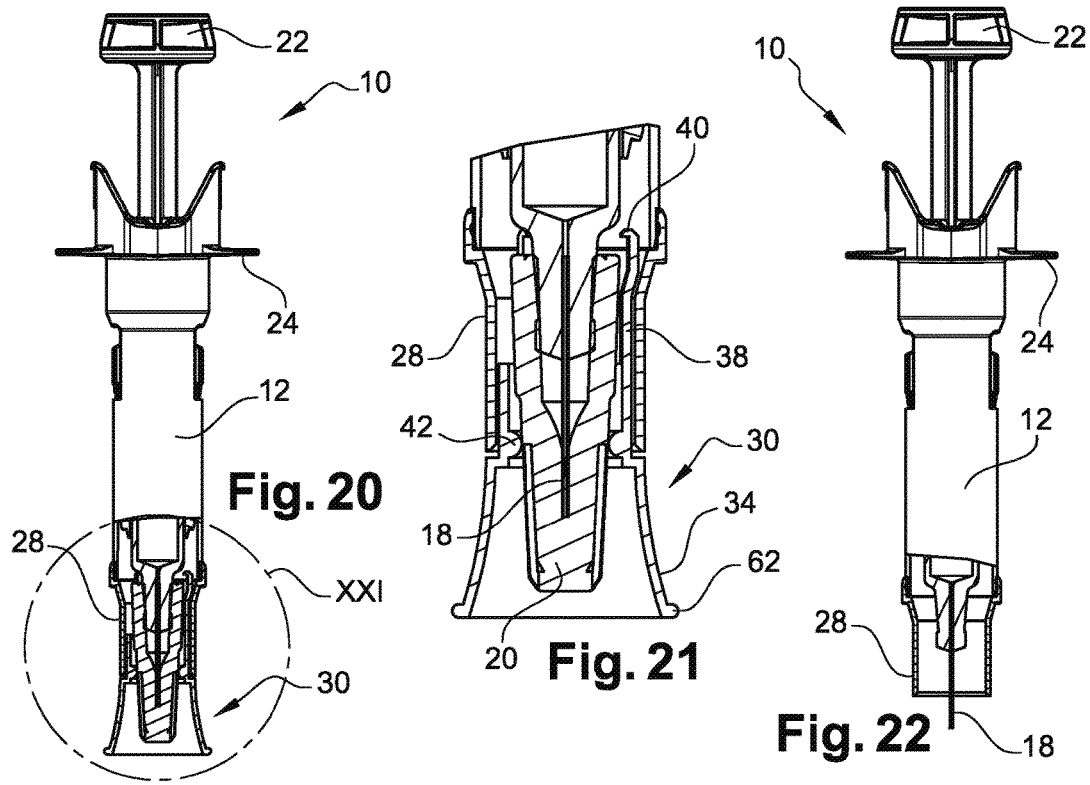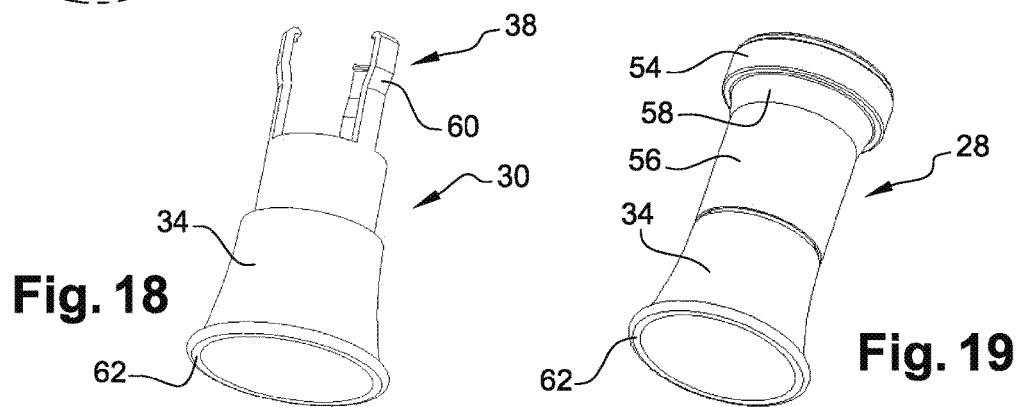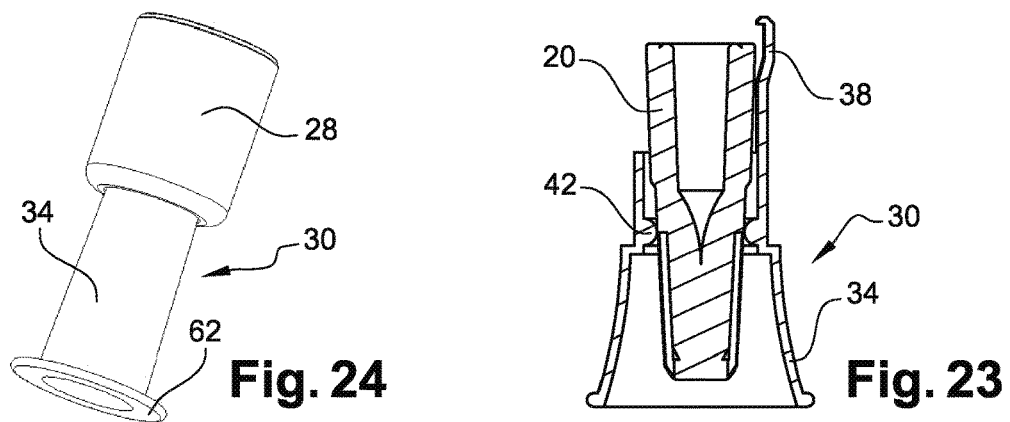

DEVICE FOR RECEIVING AN INJECTION SYRINGE COMPRISING A PROTECTIVE CAP FOR THE NEEDLE

FIELD OF THE INVENTION

The invention relates to receiving devices for an injection syringe for liquid, in particular for a pre-filled injection syringe, in particular safety devices for an injection syringe.

BACKGROUND OF THE INVENTION

The document FR 2 830 765 has already disclosed a safety device forming a receiving device for a pre-filled injection syringe provided with a needle, having an injection syringe support mounted so as to be able to slide, with respect to a protective sheath, between an injection configuration and a needle protection configuration. The pre-filled injection syringe mounted in the safety device is provided with a cap for protecting the needle before use of the injection syringe. Therefore, before the injection, the cap has to be withdrawn from the injection syringe.

The gripping surface of the cap may be of a relatively small size and, consequently, the cap may be difficult to withdraw, particularly for persons with arthritis. More generally, the same problem may be encountered, particularly for any device for receiving a syringe, in which the injection syringe is lodged, the receiving device for this purpose having dimensions greater than those of the syringe and having shapes making it easier to grip and use the injection syringe.

SUMMARY OF THE INVENTION

The object of the invention is in particular to make available a receiving device which is easier to handle.

To this end, the subject matter of the invention is a receiving device for an injection syringe, configured to receive an injection syringe comprising a needle and a protective cap for the needle, the receiving device having a distal end and comprising a removal member serving to remove the protective cap and being removably fastened to the distal end of the receiving device, the removal member comprising gripping means for gripping by a user, and catching means for catching on the cap which are able to entrain the cap when the removal member is withdrawn from the receiving device, in such a way as to expose the needle. Once exposed, at least a part of the needle protrudes from the receiving device and is ready to be introduced into the injection site.

Thus, it is proposed to arrange a removal member on the receiving device, which removal member is capable of being rigidly connected to the protective cap, such that the removal of this member causes the removal of the protective cap. As this removal member is provided with gripping means, the grip surface available to the user can be enlarged or provided with effective means for facilitating the removal. This is particularly advantageous for certain patients, for example those suffering from arthritis.

It will be noted that the receiving device can be a simple sleeve, for example forming an injection syringe support, having shapes and dimensions making it easier to hold the injection syringe, the injection syringe being intended to be fastened permanently in this sleeve. The receiving device can likewise be a sleeve forming a protective sheath for the needle.

Advantageously, the receiving device is a safety device preferably having a protective sheath for the needle, mounted slidably with respect to a syringe support, generally in the form of a sleeve, between an injection position, in which the needle protrudes from the sheath, and a protection position, in which the needle is covered by the protective sheath. The protective sheath can be arranged inside or outside the syringe support and can be in the form of an extensible sheath or a sheath into which the injection syringe retracts. The protective sheath or the syringe support generally have a support surface for the user's fingers, allowing the user to place his index finger and middle finger around the protective sheath or the syringe support.

The receiving device can additionally have one or more of the following features, alone or in combination.

The receiving device preferably comprises a plastics material.

The receiving device preferably comprises, at its distal end, an attached member called an end member, the removal member being fastened removably to this end member. When the receiving device has such an end member, the part of the cap of the injection syringe accessible to the user, when the injection syringe is mounted in the receiving device, is reduced by virtue of the fact that the end member can partially cover the cap of the injection syringe. The removal member is thus particularly advantageous since it allows the cap to be withdrawn more easily from the injection syringe, in particular when the receiving device is provided with an end member. According to one particular advantage, the end member can be configured to come into abutment against the patient's skin upon use of the injection syringe in the receiving device, thus making it possible to control the depth of penetration of the needle into the patient's body. Since this end member is attached to the rest of the receiving device, it is possible to modify the depth of penetration of the needle into the patient's body by modifying the length of the end member, without making any modification to the rest of the receiving device. This configuration thus permits the use of standard components. Moreover, according to another advantage, this end member, being attached to the receiving device, can be produced separately from the rest of the receiving device. This has the effect of facilitating the production of the receiving device, in particular the demolding operations. Indeed, certain difficulties concerning removal from the mold via the distal end of the receiving device are resolved given that the end member is generally attached to this distal end after this demolding. There is therefore the possibility of the receiving device having more complex shapes. The distal end of the receiving device, to which the end member is attached, preferably has an open cylindrical shape. The end member likewise preferably has a simple shape, for example a cylindrical overall shape, which permits simple demolding. According to yet another advantage of this configuration, when the receiving device is a safety device comprising a protective sheath, and when the end member is attached to this protective sheath, the end member makes it possible in particular to reduce the diameter of the distal end of the protective sheath, in such a way as to avoid one of the user's fingers entering the protective sheath when the latter is in the needle protection position. The end member is preferably mounted on a protective sheath of the needle.

Advantageously, the removal member and the end member are connected to each other by breakable means. By virtue of the breakable means, the user is able to easily ascertain that the receiving device and the injection syringe contained therein have not been used. It is thus possible in particular to ascertain that the injection syringe is sterile and that the dose to be delivered is complete.

According to one variant, the removal member and the end member are connected to each other by mechanical clamping. Thus, the removal member is fastened to the end member in a simple way, and it is thus possible to use different types of end members with one and the same type of removal member. Conversely, it is possible to use different types of removal members with one and the same type of end member. This provides greater flexibility of the receiving device, while at the same time making it possible to use certain standard components. In addition, provision can be made to produce receiving devices with a removal member and other ones without a removal member.

Advantageously, the catching means comprise a tab which is deformable between a configuration for catching the cap and a configuration for insertion of the cap into the removal member. Thus, the injection syringe provided with the cap can be easily and simply inserted into the receiving device, for example into the syringe support, in such a way that, after this insertion, the tab adopts the configuration for catching the cap. For example, the tab can be deformed, more precisely can be passed with force, during the introduction of the injection syringe into the receiving device, that is to say during the introduction of the cap into the removal member, and, under the effect of its inherent elasticity, it can adopt its configuration for catching the cap after introduction of the injection syringe into the receiving device. According to another embodiment, the tab may be non-deformed or slightly deformed in the configuration for insertion of the injection syringe, hence insertion of the cap into the removal member, and more deformed in the configuration for catching the cap, that is to say when the removal member is pulled in order to withdraw the cap.

The catching means preferably comprise several deformable tabs, for example two diametrically opposite deformable tabs formed on the circumference of the proximal part of the removal member, or three deformable tabs distributed about the circumference of the proximal part of the removal member. The cap is thus effectively caught by the deformable tabs at two or three different points of its periphery and can thus be withdrawn reliably from the receiving device.

The removal member can likewise comprise means for securing the protective cap in the removal member, in such a way as to rigidly connect the cap and the removal member to each other when the removal member is withdrawn from the receiving device, said securing means comprising, for example, an annular bead protruding from an inner surface of the removal member. The securing means make it possible to rigidly connect the cap and the removal member after removal of the cap. Thus, after removal of the cap, the cap cannot leave the removal member, and the user has in his hand a single piece comprising the cap and the removal member. It will be noted that the annular bead, when seen in longitudinal section, can have a rounded cross section or an angular cross section. It will furthermore be noted that the securing means are preferably distinct from the catching means. They can, however, comprise these.

Advantageously, the deformable tab has a free proximal end with a lug for retaining the cap. The retaining lug is a simple and effective means of catching the cap and can also serve as securing means. In this configuration, the securing means and the catching means are in part in common.

Advantageously, the means for securing the protective cap in the removal member comprise a ring that can cooperate with the catching means and that can be entrained out of the receiving device when the removal member is withdrawn from the receiving device. The ring can, for example, be mounted beforehand in the end member before the rest of the removal member is inserted. When the removal member is withdrawn, the catching means, for example the deformable tabs, are able to catch on the cap from the inside and on the ring from the outside in order to entrain them out of the receiving device. The catching means, being encircled by the ring, are able to maintain their hold on the cap and thus secure it inside the removal member. Thus, by virtue of the cooperation between the ring, which is a simple and standard mechanical part, and the catching means, it is possible for the protective cap to be secured in the removal member in a simple and effective manner.

The gripping means preferably have a shape flared in the distal direction of the receiving device. Thus, the dimensions of the gripping means increase in the distal direction, which makes gripping by the user easier.

The gripping means can comprise anti-slip means, for example raised elements carried by an outer surface of the removal member or an annular protuberance carried by the removal member. Advantageously, the annular protuberance is carried by a distal end of the removal member. The user thus has an improved and more accessible grip on the removal member and is able to more easily separate the removal member from the rest of the receiving device.

Advantageously, the end member likewise comprises anti-slip means.

The subject matter of the invention is also an assembly composed of a receiving device, as defined above, and of an injection syringe comprising a needle and a protective cap for the needle.

The receiving device advantageously comprises, at its distal end, an attached member called an end member, the removal member being fastened removably to this end member, the end member covering a part of the length of the needle protruding beyond the endpiece of the injection syringe, the end member being thus able to bear on the injection site in order to limit the depth of insertion of the needle.

The subject matter of the invention is also a method for assembly of a receiving device as defined above and an injection syringe comprising a needle and a protective cap for the needle, the method comprising the following steps:
  the removal member is firstly fastened to the distal end of the receiving device, and
  the injection syringe provided with the cap is inserted into the receiving device, via a proximal end of the receiving device, such that the cap becomes rigidly connected to the removal member.

A particular advantage of this method lies in the fact that the removal member is assembled in the receiving device independently of and before the injection syringe provided with the cap. Thus, the assembly of the receiving device, including the removal member, can be carried out in full before delivery to a laboratory responsible for inserting the injection syringe.

It is understood that the removal member can be fastened to the distal end of the receiving device via an end member, in which case the assembly method more precisely comprises a step during which the removal member is fastened to the end member and a step during which the assembly is attached to the receiving device.

BRIEF DESCRIPTION OF THE DRAWINGS

Embodiments of the invention will now be described solely by way of example and with reference to the attached drawings, in which:

FIGS. 1 and 2 are a perspective side view and a longitudinal sectional view, respectively, of a receiving device according to a first embodiment, FIG. 3 is a partially sectional view of the receiving device from FIG. 1 and of an injection syringe comprising a needle and a protective cap for the needle, FIG. 4 is an enlarged view of a part of FIG. 3, FIG. 5 is a view similar to that of FIG. 3, after removal of the removal member and of the cap, FIG. 6 is a sectional view of the cap and of the removal member, after they have been withdrawn from the receiving device of FIG. 3, FIGS. 7 to 10 are views similar to those of FIGS. 3 to 6 and show a receiving device according to a second embodiment, FIGS. 11 and 12 are partial sectional views of a receiving device according to a third and a fourth embodiment, FIGS. 13 and 14 are a perspective side view and a longitudinal sectional view, respectively, of a receiving device according to a fifth embodiment, FIGS. 15 to 17 are views similar to FIGS. 3 to 5 and show the receiving device according to the fifth embodiment, depicting the start of the removal of the removal member, FIGS. 18 and 19 are perspective side views, respectively, of the removal member on its own and of the removal member fastened to the end member of the receiving device according to the fifth embodiment, FIGS. 20 to 23 are views similar to FIGS. 3 to 6 and show a receiving device according to a sixth embodiment, FIG. 24 is a perspective view of the removal member fastened to the end member of a receiving device according to a seventh embodiment.

DETAILED DESCRIPTION OF THE INVENTION

Figures 25, 26:
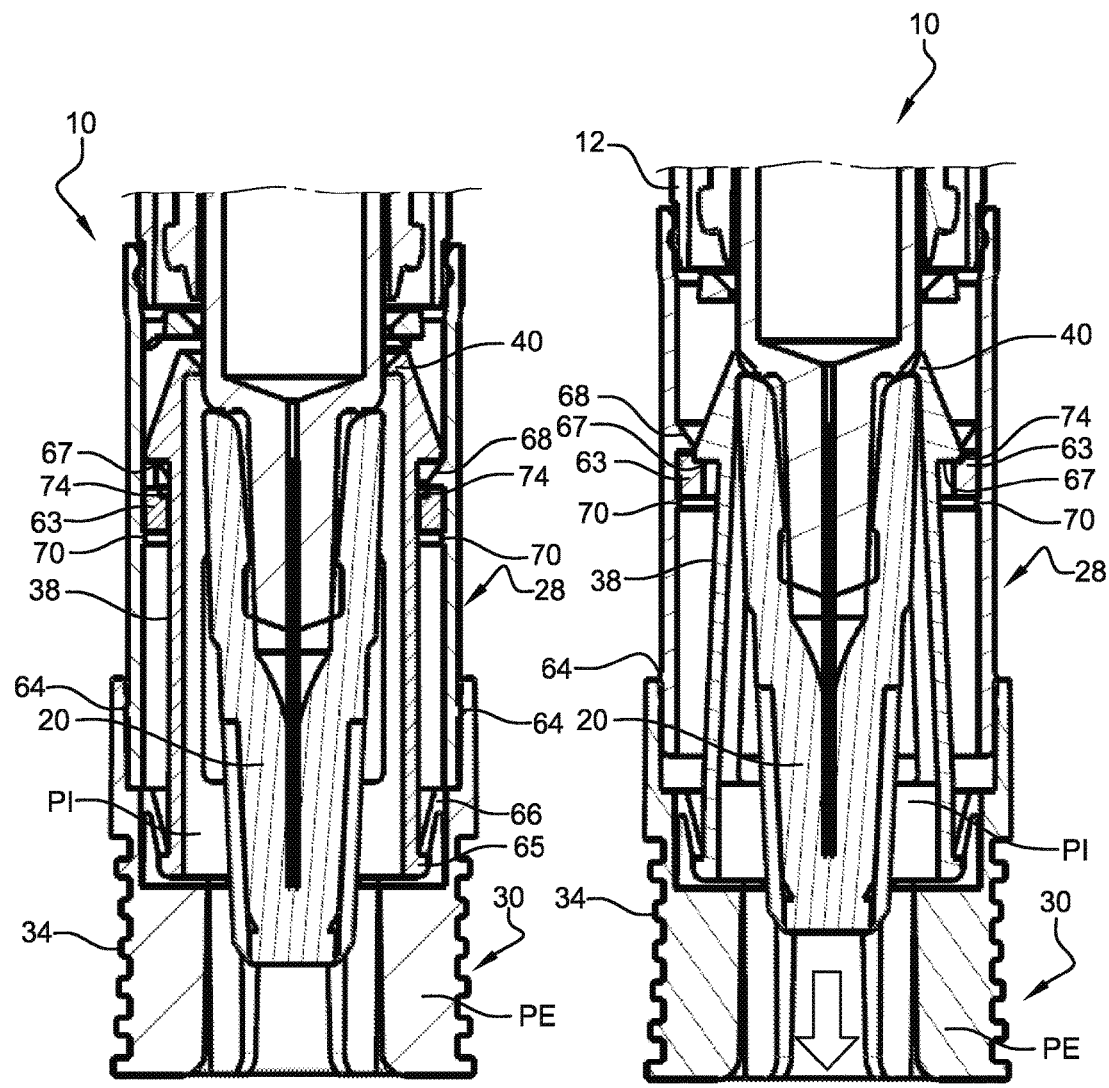
FIGS. 25 and 26 are longitudinal sectional views of a receiving device according to an eighth embodiment.

A receiving device according to a first embodiment will be described with reference to FIGS. 1 to 6.

The receiving device 10 for an injection syringe is a safety device 10 comprising a protective sheath 12, mounted slidably with respect to a syringe support 14, generally in the form of a sleeve. At its distal end, the injection syringe 16 comprises a needle 18 and a protective cap 20 for the needle. The cap 20 is attached directly to the injection syringe 16, generally by mechanical clamping. In this example, the injection syringe 16 is made of glass and is intended to be pre-filled and disposable after use. It likewise comprises a piston stem 22 configured to cooperate with the safety device 10.

The protective sheath 12 is arranged outside the syringe support 14 and is in the form of a tubular sheath into which the injection syringe 16 retracts. The protective sheath 12 is mounted so as to slide around the syringe support 14 between an injection position, in which the needle 18 protrudes from the protective sheath 12, and a protection position, in which the needle 18 is covered by the protective sheath 12. Furthermore, the protective sheath 12 has a finger rest surface 24 for the user, allowing the user to place the index finger and middle finger around the protective sheath 12.

The safety device 10 likewise comprises an end member 28, with a cylindrical overall shape, and a removal member 30 for removing the cap 20. More precisely, the protective sheath 12 comprises a distal end 26 to which the end member 28 and the removal member 30 are attached.

In this example, the end member 28 and the removal member 30 are connected to each other by breakable means 32. The removal member 30 can be withdrawn from the end member 28 after the breakable means 32 have been broken. Thus, the removal member 30 is fastened removably to the end member 28.

The end member 28 comprises raised elements 48 forming anti-slip means.

As can be seen from FIG. 3, the presence of the end member 28 reduces the grip surface area of the cap 20. It will thus be appreciated that it is particularly advantageous that the safety device 10 comprises the removal member 30 in order to be able to easily withdraw the cap 20.

The removal member 30 comprises gripping means 34 to be gripped by a user, and catching means 36 on the cap 20.

The gripping means 34 are presented here in the form of a truncated skirt that flares slightly in the distal direction, that is to say the diameter of the skirt increases in the distal direction. The gripping means 34 have a user grip surface that is larger in relation to the grip surface of the cap 20. As is shown in FIG. 1, the gripping means 34 furthermore comprise, in this example, raised elements 50 forming anti-slip means. Thus, the user's hand does not slip on the gripping means 34, and the cap 20 is withdrawn easily from the safety device 10.

The catching means 36 comprise two deformable tabs 38, which are deformable between a configuration for catching the cap 20, as seen in particular in FIG. 4, and a configuration for insertion of the cap 20 into the removal member 30. Each deformable tab 38 extends proximally from the proximal part of the gripping means 34 and has a free proximal end with a retaining lug 40 for the cap 20. The retaining lug 40 comprises a retaining face 44 for the cap 20, which retaining face 44 is perpendicular to the direction of insertion of the injection syringe 16 into the safety device 10, and an insertion face 46 for insertion of the injection syringe 16 into the safety device 10.

The removal member 30 likewise comprises a continuous annular bead 42 protruding from an inner surface of the removal member 30. As can be seen in particular in FIG. 4, in a longitudinal sectional view, the annular bead 42 has a rounded cross section when it is seen from the inside of the removal member 30. The annular bead 42 forms means for securing the cap 20 in the removal member 30 in such a way as to rigidly connect the cap 20 and the removal member 30 to each other when the removal member 30 is withdrawn from the safety device 10.

It will be noted that the annular bead 42 may optionally not be in contact with the cap 20 before removal of the cap 20. When the removal member 30 and the cap 20 are fully withdrawn from the safety device 10, the internal diameter of the annular bead 42 being less than the diameter of at least part of the cap 20, the cap 20 is rigidly connected to the removal member 30. Thus, the function of rigidly connecting the cap 20 and the removal member 30 is provided by the retaining lugs 40 and the annular bead 42, after the removal of the cap 20 and of the removal member 30 from the safety device. The connecting means likewise comprise the catching means 36.

A method for assembling the safety device 10 and the injection syringe 16 will now be described.

Firstly, the syringe support 14 is mounted inside the protective sheath 12, from the direction of the proximal end of the protective sheath 12, by placing between them a spring 52, in the compressed state, which allows the safety device 10 to convert from the injection position to the protection position.

The assembly formed by the end member 28 and the removal member 30 is then fitted on the distal end of the protective sheath 12. The removal member 30 is thus fastened removably to the distal end 26 of the safety device 10. A pre-assembled safety device 10 is thus obtained.

The injection syringe 16 provided with the cap 20 is then inserted through the proximal end of the safety device 10. This step can advantageously take place in a factory other than that in which the safety device 10 is assembled, especially when the injection syringe 16 is pre-filled.

When the cap 20 comes into contact with the insertion faces 46 carried by the retaining lugs 40 of the proximal free ends of the deformable tabs 38, the deformable tabs 38 deform radially in order to adopt their configuration for insertion of the cap 20 into the removal member 30.

Once the injection syringe 16 has been fully inserted into the safety device 10, the cap 20 is inserted into the removal member 30 and the deformable tabs 38, under the effect of their inherent elasticity, adopt their configuration for catching the cap 20, that is to say the retaining faces 44 come into engagement with the cap 20. In their catching configuration, the catching means 36 then make it possible to entrain the cap 20 when the removal member 30 is withdrawn from the safety device 10 in such a way as to expose the needle 18. In addition, the cap 20 is likewise secured in the removal member 30 by virtue of the annular bead 42.

As can be seen from FIGS. 3 and 4, the removal member 30, in particular the gripping means 34 thereof, has a grip surface that is larger in relation to the grip surface of the cap 20.

The safety device 10 and the injection syringe 16 are ready for use.

When the user wishes to inject a product contained in the injection syringe 16, he picks up the safety device 10. He takes the end member 28 in one hand and takes the removal member 30 in the other hand via the gripping means 34. He pivots the end member 28 with respect to the removal member 30 in order to break the breakable means 32.

The user then pulls the removal member 30 in the distal direction in order to withdraw the removal member 30 from the safety device 10. By virtue of the lugs 40, the removal member 30 entrains the cap 20.

As is shown in FIG. 6, when the removal member 30 is fully withdrawn from the safety device 10, the cap 20 remains in the removal member 30 since it is sandwiched between the retaining lugs 40 and the annular bead 42. The cap 20 is thus rigidly connected to the removal member 30.

The injection syringe 16 is ready to be used. As can be seen from FIG. 5, the end member 28 serves as an abutment against the patient's skin, and the needle 18 can be introduced into the patient by the length protruding from the end member 28.

When the injection is completed, the protective sheath 12, under the effect of the spring 52, adopts its position of protection of the needle 18, with the syringe support 14 and the injection syringe 16 being retracted inside the protective sheath 12. The needle 18 is then inaccessible, and the risk of a user sustaining an injury on the needle 18 is virtually zero. It will be noted that the end member 28 advantageously has a closed distal end, or its opening has a reduced diameter, such that a user's finger cannot come into contact with the needle 18 once the protective sheath 12 is in the protection position.

In the text below, the elements that the different embodiments have in common are identified by the same reference numbers. Only the main differences are described; it will be noted that the other elements are similar.

A second embodiment of the receiving device 10, shown in FIGS. 7 to 10, is similar to the first embodiment.

It differs from the latter in that the end member 28 is shorter, and therefore the grip surface of the cap 20 is larger than in the preceding embodiment. However, the cap 20 can be difficult to withdraw all the same.

In this embodiment, the gripping means 34 of the removal member 30 likewise comprise deformable tabs 38. Furthermore, the skirt forming the distal part of the gripping means 34 is more flared than in the first embodiment and allows the user a good grip.

As is shown in FIG. 9, the needle 18 protrudes fully from the safety device 10 when the protective sheath 12 is in the injection position.

A third embodiment of the receiving device 10, shown in FIG. 11, is similar to the second embodiment. It differs from the latter in that the shape of the removal member 30 is similar to the shape of the removal member 30 of the first embodiment.

A fourth embodiment of the receiving device 10, shown in FIG. 12, is similar to the first embodiment. It differs from the latter in that the shape of the removal member 30 is similar to the shape of the removal member 30 of the second embodiment. Moreover, the removal member 30 has a distal wall 57 which at least partially occludes its distal end. If, after removal of the removal member 30 and of the cap 20, the cap 20 were thus to disengage from the annular bead 42, the cap 20 remains wedged between the distal wall 57 and the retaining lugs 44.

A fifth embodiment of the receiving device 10 is described with reference to FIGS. 13 to 19.

This embodiment is similar to the previously described embodiments. It differs from these particularly in that the end member 28 and the removal member 30 are connected to each other by mechanical clamping.

Moreover, the removal member 30 has three deformable tabs 38 distributed about the circumference of the proximal part of the removal member 30, and four annular beads 42 protruding from the inner surface of the removal member 30. At their distal end, the gripping means 34 of the removal member 30 likewise comprise an annular protuberance 62 that forms anti-slip means. When the user pulls on the removal member 30, his hand is blocked by the annular protuberance 62.

As is shown in FIGS. 14 and 16, in longitudinal section, the annular beads 42 have an angular cross section when viewed from the inside of the removal member 30. These annular beads 42 form means for securing the cap 20 in the removal member 30 in such a way as to rigidly connect the cap 20 and the removal member 30 to each other when the removal member 30 is withdrawn from the safety device 10. In this embodiment, the securing means are distinct from the catching means 36.

As is shown in FIG. 18, the free proximal end of each deformable tab 38 has a ramp 60 extending radially outward of the safety device 10 such that, in their non-deformed state, the retaining lug 40 carried by each deformable tab 38 does not interfere with the cap 20 when the latter is inserted into the safety device 10. Thus, in the state in which they are not elastically deformed, the deformable tabs 38 are in the configuration for insertion of the cap 20 into the removal member 30, as is shown in FIG. 14.

The end member 28 comprises a proximal part 54 attached to the protective sheath 12 and a distal part 56 receiving the removal member 30, these being shown in FIG. 19. With the distal part 56 having a diameter smaller than that of the proximal part 54, the proximal and distal parts 54, 56 are connected to each other via a median part 58 that forms the transition between the diameters of the proximal and distal parts 54, 56.

The method of assembly is similar to that previously described.

Thus, once the removal member 30 has been fastened on the end member 28 by mechanical clamping, the assembly is attached to the protective sheath 12.

Upon insertion of the injection syringe 16 provided with the cap 20 into the safety device 10, the cap 20 is rigidly connected to the removal member 30 by radial mechanical clamping of the annular beads 42 on the cap 20, the deformable tabs 38 being in the configuration for insertion of the cap 20 into the removal member 30.

In order to inject the product contained in the injection syringe 16, the user picks up the safety device 10. He takes the end member 28 in one hand and takes the removal member 30 in the other hand via the gripping means 34. He pulls the removal member 30 in the distal direction, his hand being kept in the distal direction by the annular protuberance 62.

During the movement of the removal member 30 with respect to the end member 28, the free proximal end of each deformable tab 38 adopts its configuration for catching the cap 20 in cooperation with the distal part 56 of the end member 28, as is shown in FIGS. 15 and 16. The retaining lugs 40 engage with the cap 20 and entrain the cap 20 along with the removal member 30, in such a way as to expose the needle 18.

A sixth embodiment of the receiving device 10 is shown in FIGS. 20 to 23 and is similar to the fifth embodiment of the receiving device 10.

It differs from the latter in that the inner surface of the removal member 30 has a single annular bead 42 which, by radial mechanical clamping, rigidly connects the cap 20 to the removal member 30. Seen in longitudinal section, the annular bead 42 has a rounded cross section when seen from the inside of the removal member 30.

As is shown in FIG. 23, when the removal member 30 and the cap 20 are completely withdrawn from the safety device 10, the deformable tabs 38 recover their insertion configuration on account of their inherent elasticity. However, by virtue of the annular bead 42, the cap 20 remains rigidly connected to the removal member 30. The same applies to the fifth embodiment.

In a seventh embodiment, shown in FIG. 24, the gripping means 34 of the removal member 30 have a widened annular protuberance 62.

An eighth embodiment of the receiving device 10 will be described with reference to FIGS. 25 and 26.

In this embodiment, the removal member 30 has three parts, namely an outer part PE, which comprises the gripping means 34, an inner part PI, which carries the deformable tabs 38, and a ring 63.

The outer part PE is fastened to the end member 28 by an outer bead 64, carried by the distal annular skirt of the end member 28, being snap-fitted into a hollow ring, with a shape matching the outer bead 64, on the inner surface of the outer part PE. The outer part PE can be fastened on the end member 28 by any suitable means. The inner part PI is fastened on the outer part PE in the area of the distal part of the deformable tabs 38. For this purpose, the inner part PI has a distal shoulder 65 bearing against the flexible tongues 66 carried by the outer part PE. Moreover, at their proximal end, the deformable tabs 38 comprise an abutment 67 which bears on an annular ramp 68 when the deformable tabs 38 are in the configuration for insertion of the cap, as is shown in FIG. 25. In this configuration, the deformable tabs 38 are not deformed or are only slightly deformed. The annular ramp 68 is carried by an inner surface of the end member 28. It protrudes from this surface and converges toward the distal part of the receiving device 10. The inner part PI can be fastened to the outer part PE by any other suitable means.

The ring 63 is snap-fitted between the annular ramp 68 and an inner bead 70 of the end member 28. The ring 63 has a recess 74.

Upon removal of the cap 20, a force applied in the direction of the arrow in FIG. 26 allows the abutment 67 to slide on the annular ramp 68. The abutment 67 is stopped by the recess 74 and thus cooperates with the ring 63. During the sliding, the deformable tab 38 deforms in order to adopt its configuration for catching the cap 20, as is shown in FIG. 26. The retaining lugs 40 come into engagement with the cap 20, which allows the latter to be entrained with the removal member 30. The cap 20 is retained in the removal member 30 by virtue of the cooperation between the ring 63 and the deformable tabs 38 and also securing means (not shown) of the outer part PE of the removal member 30.

The ring 63 makes it possible to hold the deformable tabs 38, which have a tendency to be returned elastically to their configuration for insertion of the cap 20. The deformable tabs 38 are thus kept deformed in their configuration for catching the cap 20. The ring 63 thus allows the cap 20 to be rigidly connected to the removal member 30.

The method of assembly is similar to that previously described.

Firstly, the ring 63 is mounted in the end member 28, between the annular ramp 68 and the inner bead 70. The inner part PI of the removal member 30 is then inserted into the end member 28 by virtue of the deformable tabs 38. The latter deform in the area of the ring 63, then the abutment 67 slides on the annular ramp 68 until it passes beyond the latter. Once the annular ramp 68 has been passed, the deformable tabs 38 adopt their configuration of insertion and hold the inner part PI on the end member 28. The outer part PE is then mounted on the end member 28 by virtue of the outer bead 64 carried by the distal annular skirt of the end member 28 and by virtue of the complementary shape on the inner surface of the outer part PE. Finally, the assembly is attached to the protective sheath 12.

The injection syringe 16 provided with the cap 20 is then inserted into the receiving device 10. The insertion is easy, because the deformable tabs 38 are in their configuration for insertion of the cap 20, in which configuration they are spaced apart from each other. They maintain this configuration after the insertion of the cap 20, thereby allowing play between the cap 20 and the deformable tabs 38.

In order to inject the product contained in the injection syringe 16, the user withdraws the cap 20 with the aid of the removal member 30, which is made easy to grip by the gripping means 34. During the movement of the removal member 30 with respect to the end member 28, the free proximal end of each deformable tab 38 adopts its configuration for catching the cap 20 by cooperation with the abutment 67, the annular ramp 68 and the recess 74 of the ring 63. The abutment 67, which was at the top of the annular ramp 68, slides along the latter until it passes beyond it and is stopped by the recess 74. The retaining lugs 40 carried by the proximal ends of the deformable tabs 38 catch on the cap 20. The deformable tabs 38 are then in their configuration for catching the cap 20, in which configuration they have come closer to each other. Thus, the distal movement of the removal member 30 brings about that of the cap 20 and of the ring 63, which comes free from the annular ramp 68, and entrains the ring 63 beyond the annular bead 70. During and after the withdrawal of the removal member 30, the ring 63 is maintained on the deformable tabs 38, which are blocked in the catching configuration by the recess 74. Thus, the cap 20 remains secured in the removal member 30.

Of course, it will be possible to make numerous modifications to the invention without departing from the scope thereof.

In particular, the receiving device 10 can have just one sleeve for receiving the injection syringe 16, or the protective sheath 12 can be received in the syringe support 14 and be in the form of an extensible protective sheath.

Moreover, the receiving device 10 may not have an end member 28, and the sleeve 14 for receiving the injection syringe 16, the syringe support 14 or the protective sheath 12 may carry anti-slip means.

The number of deformable tabs 38 and the number of annular beads 42 are given merely by way of example. Furthermore, the annular bead 42 may not continue about the entire circumference of the inner surface of the removal member 30. Moreover, the cross section of the annular bead can have shapes other than those described, and the securing means can have a form other than that of an annular bead.

Furthermore, the features of the different embodiments can be combined with one another.

The invention claimed is:

1. A receiving device for an injection syringe, configured to receive an injection syringe comprising a needle and a protective cap for the needle, the receiving device having a distal end and being characterized in that it comprises a removal member serving to remove the protective cap and being removably fastened to the distal end of the receiving device, the removal member comprising a gripping section for gripping by a user, and a catch for catching on the cap, which are able to entrain the cap when the removal member is withdrawn from the receiving device, in such a way as to expose the needle, wherein the catch comprises deformable tabs each having a retaining lug;
   the receiving device further comprising a part in the form of a ring extending around outside surfaces of the deformable tabs, wherein the part can cooperate with the deformable tabs to secure the protective cap in the removal member by deforming the deformable tabs inward against the protective cap and the part is withdrawn from the receiving device when the removal member is withdrawn from the receiving device;
   wherein the part is distinct from the gripping section;
   wherein, when the removal member is fastened to the distal end of the receiving device, the part and the deformable tabs are movable with respect to one another from a first position, to a second position in which the part is maintained against the outside surfaces of the deformable tabs and deforms the deformable tabs inward against the protective cap.

2. The receiving device as claimed in claim 1, in which the receiving device is a safety device having a protective sheath for the needle.

3. The receiving device as claimed in claim 1, in which the receiving device comprises, at its distal end, an attached member called an end member, the removal member being fastened removably to this end member.

4. An assembly comprising a receiving device as claimed in claim 3, wherein the end member covers a part of a length of the needle protruding beyond an end piece of the injection syringe, the end member being thus able to bear on the injection site in order to limit a depth of insertion of the needle.

5. The receiving device as claimed in claim 1, in which the gripping section comprises an anti-slip element.

6. The receiving device as claimed in claim 5, wherein the anti-slip element includes raised elements carried by an outer surface of the removal member.

7. An assembly comprising a receiving device as claimed in claim 1 and the injection syringe comprising the needle and the protective cap for the needle.

8. A method for assembly of a receiving device as claimed in claim 1 and of an injection syringe comprising the needle and the protective cap for the needle, the method being characterized in that it comprises the following steps:
   the removal member is firstly fastened to the distal end of the receiving device, and
   the injection syringe provided with the protective cap is inserted into the receiving device, via a proximal end of the receiving device, such that the protective cap becomes rigidly connected to the removal member.

9. A receiving device for an injection syringe, configured to receive an injection syringe comprising a needle and a protective cap for the needle, comprising:
   a sheath for receiving the injection syringe, the sheath having a distal end;
   a removal member serving to remove the protective cap and being removably fastened to the distal end of the sheath, the removal member comprising a gripping section for gripping by a user, and a catch for catching on the cap, which is able to entrain the cap when the removal member is withdrawn from the receiving device, in such a way as to expose the needle;
   wherein the catch comprises deformable tabs each having a retaining lug;
   wherein the removal member comprises a ring positioned adjacent to outside surfaces of the deformable tabs for securing the protective cap in the removal member, in such a way as to rigidly connect the cap and the removal member to each other when the removal member is withdrawn from the receiving device, the ring being distinct from the gripping section and the catch;
   wherein, when the removal member is fastened to the distal end of the sheath, the ring and deformable tabs are movable with respect to one another from a first position, to a second position in which the ring is maintained against the outside surfaces of the deformable tabs and deforms the deformable tabs inward against the protective cap.

10. The receiving device as claimed in claim 9, wherein the distal end sheath comprises an end member attached thereto, the removal member being removably fastened to the end member.

11. An assembly comprising a receiving device as claimed in claim 10, wherein the end member covers a part of a length of the needle protruding beyond an end piece of the injection syringe, the end member being thus able to bear on the injection site in order to limit the depth of insertion of a needle.

12. The receiving device as claimed in claim 9, in which the gripping section comprises an anti-slip element.

13. The receiving device as claimed in claim 12, wherein the anti-slip element includes raised elements carried by an outer surface of the removal member.

14. An assembly comprising a receiving device as claimed in claim 9 and the injection syringe comprising the needle and the protective cap for the needle.

15. A method for assembly of a receiving device as claimed in claim 9 and of the injection syringe comprising the needle and the protective cap for the needle, the method being characterized in that it comprises the following steps:
- the removal member is firstly fastened to the distal end of the sheath, and
- the injection syringe provided with the protective cap is inserted into the sheath, via a proximal end of the sheath, such that the protective cap becomes rigidly connected to the removal member.

* * * * *